United States Patent
Venugopal et al.

(10) Patent No.: US 10,438,355 B2
(45) Date of Patent: Oct. 8, 2019

(54) SYSTEM AND METHOD FOR ESTIMATING ARTERIAL PULSE WAVE VELOCITY

(71) Applicant: General Electric Company, Schenectady, NY (US)

(72) Inventors: Prem Venugopal, Clifton Park, NY (US); Thomas Kwok-Fah Foo, Clifton Park, NY (US); Christopher Judson Hardy, Niskayuna, NY (US); Ek Tsoon Tan, Mechanicville, NY (US)

(73) Assignee: General Electric Company, Schenectady, NY (US)

( * ) Notice: Subject to any disclaimer, the term of this patent is extended or adjusted under 35 U.S.C. 154(b) by 929 days.

(21) Appl. No.: 14/936,903

(22) Filed: Nov. 10, 2015

(65) Prior Publication Data

US 2017/0132788 A1    May 11, 2017

(51) Int. Cl.
*A61B 6/00* (2006.01)
*G06T 7/00* (2017.01)
(Continued)

(52) U.S. Cl.
CPC ............ *G06T 7/0014* (2013.01); *A61B 5/022* (2013.01); *A61B 5/026* (2013.01);
(Continued)

(58) Field of Classification Search
CPC ....... G06T 7/0014; G06T 7/62; G61B 5/0285; G61B 5/022
See application file for complete search history.

(56) References Cited

U.S. PATENT DOCUMENTS

| 6,113,543 A | 9/2000 | Bonnefous |
| 6,117,087 A | 9/2000 | Kamm et al. |

(Continued)

FOREIGN PATENT DOCUMENTS

| WO | 2000/076394 A1 | 12/2000 |
| WO | 2013110929 A1 | 8/2013 |

OTHER PUBLICATIONS

Hoctor, R.T. et al., "Array signal processing for local arterial pulse wave velocity measurement using ultrasound," IEEE Transactions on Ultrasonics, Ferroelectrics, and Frequency Control, vol. 54, Issue 5, pp. 1018-1027, (2007) (Abstract).

(Continued)

*Primary Examiner* — Joseph M Santos Rodriguez

(57) ABSTRACT

A method for determining an arterial pulse wave velocity representative of a health condition of a blood vessel includes receiving an image data set comprising a plurality of images of a subject, from an imaging modality. The method also involves determining a blood vessel region in an image from the plurality of images. The method further includes determining a plurality of cross-sectional area values of a blood vessel at a plurality of locations in the blood vessel region, corresponding to a plurality of phases of a cardiac cycle of the subject and determining a plurality of flow rate values of blood flowing in the blood vessel corresponding to the plurality of cross-sectional area values. The method also includes determining a hemodynamic model based on the plurality of cross-sectional area values and the plurality of blood flow rate values and determining the arterial pulse wave velocity based on the hemodynamic model.

19 Claims, 10 Drawing Sheets

(51) Int. Cl.
*A61B 5/02* (2006.01)
*A61B 5/022* (2006.01)
*A61B 5/026* (2006.01)
*A61B 5/055* (2006.01)
*A61B 5/00* (2006.01)
*A61B 5/0285* (2006.01)
*G06T 7/11* (2017.01)
*G06T 7/62* (2017.01)
*G16H 50/30* (2018.01)
*G16H 30/40* (2018.01)

(52) U.S. Cl.
CPC ........ *A61B 5/02007* (2013.01); *A61B 5/0285* (2013.01); *A61B 5/055* (2013.01); *A61B 5/7275* (2013.01); *G06T 7/11* (2017.01); *G06T 7/62* (2017.01); *G16H 30/40* (2018.01); *G16H 50/30* (2018.01); *G06T 2207/10088* (2013.01); *G06T 2207/30104* (2013.01)

(56) References Cited

U.S. PATENT DOCUMENTS

| | | | |
|---|---|---|---|
| 7,191,110 | B1 | 3/2007 | Charbel et al. |
| 7,621,876 | B2 | 11/2009 | Hoctor et al. |
| 2005/0143640 | A1 | 6/2005 | Hoctor et al. |
| 2006/0211942 | A1 | 9/2006 | Hoctor et al. |
| 2009/0005691 | A1* | 1/2009 | Huang ............. A61B 3/102 600/476 |
| 2010/0017171 | A1 | 1/2010 | Spilker et al. |
| 2010/0241011 | A1 | 9/2010 | McCombie et al. |
| 2011/0060576 | A1* | 3/2011 | Sharma ............. G06T 7/0012 703/11 |
| 2013/0243294 | A1 | 9/2013 | Ralovich et al. |
| 2014/0236547 | A1 | 8/2014 | Itu et al. |
| 2014/0343424 | A1 | 11/2014 | Konofagou et al. |
| 2015/0238095 | A1 | 8/2015 | Lading et al. |
| 2015/0282718 | A1* | 10/2015 | Wiard ............. A61B 5/02125 600/483 |

OTHER PUBLICATIONS

International Search Report and Written Opinion issued in connection with corresponding PCT Application No. PCT/US2016/061070 dated Feb. 14, 2017.

Bolster, Jr., "Accuracy of Arterial Pulse-Wave Velocity Measurement Using MR", Journal of Magnetic Resonance Imaging, vol. 8, Issue 4, pp. 878-888, 1998.

Alastruey et al., "Lumped Parameter Outflow Models for 1-D Blood Flow Simulations: Effect on Pulse Waves and Parameter Estimation", Communications in Computational Physics, vol. 4, Issue 2, pp. 317-336, Aug. 2008.

Van De Vosse et al., "Pulse Wave Propagation in the Arterial Tree", Annual Review: Fluid Mechanics, vol. 43, pp. 467-499, 2011.

Wentland et al., "Review of MRI-Based Measurements of Pulse Wave Velocity: A Biomarker of Arterial Stiffness", Cardiovascular Diagnosis and Therapy, vol. 4, Issue 2, pp. 193-206, Apr. 2014.

* cited by examiner

SYSTEM AND METHOD FOR ESTIMATING ARTERIAL PULSE WAVE VELOCITY

BACKGROUND

Embodiments of the present invention relate generally to determination of arterial stiffness indicative of medical conditions, and more particularly to systems and methods for estimation of arterial pulse wave velocity based on a hemodynamic model.

Atherosclerosis is referred to narrowing and stiffening of blood artery associated with deposition of fat inside the arterial walls. Arterial stiffness provides an indication of a number of medical conditions such as diabetes and hypertension. Determination of arterial stiffness provides an indication of a medical condition and progression of disease. In some instances, treatment options may be determined based on the arterial stiffness.

When the heart beats, a pulse is transmitted through the arterial system. The pulse wave propagates through the arterial system by distending the elastic walls of the arteries. Arterial pulse velocity is mathematically similar to phase velocity of electrical waves propagating in a cable or transmission line. The arterial wave equation is characterized by compliance of the artery, inertia of blood, and blood viscous resistance which corresponds to capacitance, inductance and resistance of the electrical wave equation.

The arterial pulse wave velocity is used to determine the stiffness of the blood vessel. One technique of estimating the arterial pulse wave velocity from blood flow data is the foot-to-foot method. Such a technique involves tracking changes in blood flow as a function of time and position along the blood vessel, and then tracking motion of a fiduciary point in the blood flow waveform as the wave propagates along the length of the blood vessel. A pulse wave velocity is estimated based on time delay between fiduciary points at two locations along the length of the blood vessel and the distance between the two locations. However, the arterial pulse wave velocity estimated by such a technique can be affected by wave reflection and by choice of the fiduciary point.

BRIEF DESCRIPTION

In accordance with one aspect of the present invention, a method is disclosed. The method includes receiving an image data set comprising a plurality of images of a subject, from an imaging modality and determining a blood vessel region in an image from the plurality of images, using an image segmentation technique. The method further includes determining a plurality of cross-sectional area values of a blood vessel at a plurality of locations in the blood vessel region, corresponding to a plurality of phases of a cardiac cycle of the subject. The method also includes determining a plurality of flow rate values of blood flowing in the blood vessel corresponding to the plurality of cross-sectional area values, based on the image data set. The method further includes determining a hemodynamic model based on the plurality of cross-sectional area values and the plurality of blood flow rate values. Further, the method includes determining an arterial pulse wave velocity based on the hemodynamic model, wherein the arterial pulse wave velocity is representative of a health condition of the blood vessel.

In accordance with another of aspect of the present invention, a system is disclosed. The system includes an imaging modality and a processor module coupled to the imaging modality and configured to receive an image data set comprising a plurality of images of a subject, from the imaging modality. The processor module is further configured to determine a blood vessel region in an image from the plurality of images, using an image segmentation technique. The processor module is further configured to determine a plurality of cross-sectional area values of a blood vessel, at a plurality of locations in the blood vessel region corresponding to a plurality of phases of a cardiac cycle of the subject. The processor module is further configured to determine a plurality of flow rate values of blood flowing in the blood vessel corresponding to the plurality of cross-sectional area values, based on the image data set. Further, the processor module is configured to determine a hemodynamic model based on the plurality of cross-sectional area values and the plurality of blood flow rate values. The processor module is also configured to determine an arterial pulse wave velocity based on the hemodynamic model, wherein the arterial pulse wave velocity is representative of a health condition of the blood vessel.

In accordance with another aspect of the present invention, a non-transitory computer readable medium having instructions to enable at least one processor module to determine an arterial pulse wave velocity representative of a health condition of the blood vessel is disclosed. The instructions enable the at least one processor module to receive an image data set comprising a plurality of images of a subject, from an imaging modality and determine a blood vessel region in an image from the plurality of images, using an image segmentation technique. Further, the instructions enable the at least one processor module to determine a plurality of cross-sectional area values of a blood vessel at a plurality of locations in the blood vessel region corresponding to a plurality phases of a cardiac cycle of the subject. Further, the instructions enable the at least one processor module to determine a plurality of flow rate values of blood flowing in the blood vessel corresponding to the plurality of cross-sectional area values, based on the image data set. The instructions also enable the at least one processor module to determine a hemodynamic model based on the plurality of cross-sectional area values and the plurality of blood flow rate values and determine the arterial pulse wave velocity based on the hemodynamic model.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

As will be described in detail hereinafter, embodiments of the present invention disclose systems and methods configured to determine arterial stiffness indicative of a plurality of medical conditions of a subject. More particularly, embodiments of the present invention disclose systems and methods configured to estimate arterial pulse wave velocity based on a hemodynamic model, where the estimated arterial pulse wave velocity is representative of a health condition of the blood vessel of the subject.

The term "flow rate" refers to a volume of fluid that passes a particular location along a blood vessel and is measured, for example, in units of cubic meters per second. The terms "blood vessel compliance" and "vessel compliance" are used equivalently and interchangeably, and relate to the ability of a hollow organ such as a blood vessel to distend and increase its volume when subjected to increased pressure on the vessel walls. The regional vessel compliance is measured as a change in the local arterial blood volume (for example, along a 1-cm length of blood vessel) per unit change in local arterial blood pressure. The term "pulse wave velocity" refers to a ratio of a distance travelled by a wave to time taken by the wave to travel the distance. The arterial pulse wave velocity is representative of a health condition of the blood vessel. The term "hemodynamic model" is referred to a fluid dynamic model related to blood flow within a circulatory system. The term "cuff measurements" refers to blood pressure measurements obtained using a cuff wrapped around an upper arm of a subject, for example. The "image data set" refers to a plurality of two-dimensional images or a three-dimensional image data set, or a four-dimensional image data set from an image modality such as magnetic resonance imaging system or a computer tomographic system, or an ultrasound imaging system.

Figure 1:
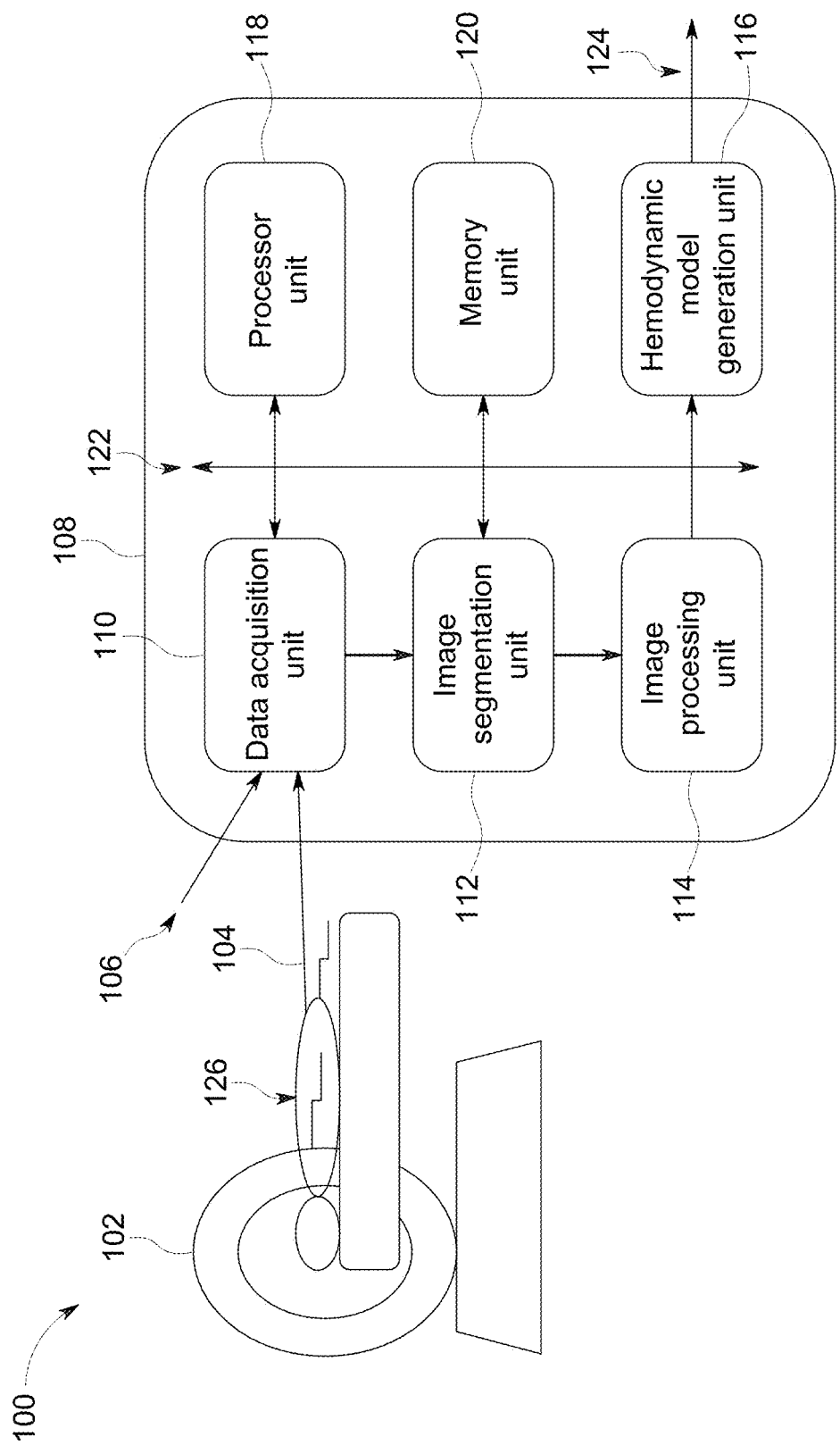
FIG. 1 is a diagrammatic illustration of a system for determining a pulse wave velocity of blood flow in accordance with an embodiment of the present invention.

FIG. 1 is a schematic representation of a system 100 having an imaging modality 102 and an arterial pulse wave velocity determination unit 108 in accordance with an exemplary embodiment of the present invention. The imaging modality 102 is configured to generate an image data set 104 of a subject 126 during medical examination. In one embodiment, the imaging modality 102 is a magnetic resonance imaging (MRI) system generating magnetic resonance image data set. In other embodiments, other imaging modalities such as, but not limited to, a magnetic resonance imaging system, a computer tomographic system or an ultrasound system are used to generate the image data set. In an embodiment where the image data set 104 is acquired from an MRI system, a velocity-phase-encoding gradient field may be used for generating the image data set 104. The term velocity-phase-encoding refers to a technique of imparting different phase shifts to protons moving at different velocities by application of a suitable bipolar-waveform gradient field prior to acquiring the magnetic resonance signal of image data set 104. In such a case, the image data set 104 includes velocity information of the functional aspects of the organs being examined. In one embodiment, the image data set 104 acquired from the MRI system includes velocity information obtained via velocity-phase-encoding gradient field along one or more directions. In one embodiment, the system 100 further includes a mechanism (not shown) to generate blood pressure values 106 from a plurality of cuff measurements obtained during examination of the subject 126. In one embodiment, the blood pressure values 106 are representative of central blood pressure values determined by modifying cuff measurements representative of peripheral blood pressure values. The system 100 further includes an arterial pulse wave velocity determination unit 108 configured to receive the image data set 104 and the plurality of blood pressure values 106 and generate an arterial pulse wave velocity 124. The arterial pulse wave velocity determination unit 108 includes a data acquisition unit 110, an image segmentation unit 112, an image processing unit 114, a model generation unit 116, a processor module 118, and a memory unit 120. A communications bus 122 is configured to provide communication between various units of the arterial pulse wave velocity determination unit 108.

The data acquisition unit 110 is communicatively coupled to the imaging modality 102 and configured to receive the image data set 104. The image data set 104 includes a plurality of images having a vessel region. The vessel region includes a blood vessel to be examined. In one embodiment, the data acquisition unit 110 is also communicatively coupled to blood pressure measuring device (not shown) having a cuff wound around a limb or arm of the subject 126 and configured to measure a plurality of cuff measurements representative of blood pressure of the subject 126. The data acquisition unit 110 is configured to perform a variety of signal conditioning processes such as noise filtering, scaling, and analog-to-digital conversion. The data acquisition unit 110 is further configured to extract one or more images of the image data set 104 and further process the extracted one or more images. In one embodiment, the data acquisition unit 110 is also configured to determine a mean blood pressure based on the plurality of cuff measurements of the subject 126.

The image segmentation unit 112 is communicatively coupled to the data acquisition unit 110 and configured to receive an image extracted from the image data set 104. The image segmentation unit 112 is further configured to determine a vessel region in the image based on an image segmentation technique. In one embodiment, the image segmentation is performed based on an image registration technique. In another embodiment, the image segmentation is performed based on a graph based technique. The image segmentation unit 112 is further configured to identify a blood vessel in the vessel region, for which a blood vessel stiffness is to be determined.

The image processing unit 114 is communicatively coupled to the image segmentation unit 112 and configured to determine a vessel centerline and a cross-sectional area of the blood vessel in the vessel region. A plurality of cross-sectional area values is determined at a plurality of locations along the length of the blood vessel corresponding to a plurality of phases of the cardiac cycle. The image processing unit 114 is further configured to determine blood flow rates in the blood vessel from the image dataset, for a plurality of phases in the cardiac cycle. In one embodiment, a plurality of blood flow rate values is determined at a plurality of locations along the blood vessel, for a plurality of phases of the cardiac cycle. A plurality of blood pressure values is calculated at a plurality of locations along the length of the blood vessel corresponding to a plurality of phases of the cardiac cycle.

The model generation unit 116 is communicatively coupled to the image processing unit 114 and configured to determine a hemodynamic model for blood flow based on the image data set 104 and the blood pressure values 106. The model generation unit 116 is further configured to determine an arterial pulse wave velocity 124 based on the hemodynamic model. In one embodiment, the hemodynamic model is a one dimensional pulse propagation model coupled to a lumped resistance-capacitance-resistance (RCR) model. In another embodiment, the hemodynamic model is a three dimensional computation fluid dynamic model coupled to the lumped RCR model. In one embodiment, the hemodynamic model is determined based on an optimization technique. In one embodiment, the lumped RCR model includes a first resistance $R_1$, a second resistance $R_2$ and a capacitance C. The capacitance C is referred herein as lumped model compliance value. In one embodiment, a genetic algorithm is used for the optimization technique. In another embodiment, a gradient descent technique is used for the optimization technique for determining arterial pulse wave velocity of the blood flow within the blood vessel. In one embodiment, determining the hemodynamic model involves determining at least one of a mean blood pressure value, a blood vessel compliance value and a lumped model compliance value based on the optimization technique.

In one embodiment, the blood vessel behavior is expressed by a linear elastic model represented by the relation:

$$p - p_0 = \beta \frac{\sqrt{A} - \sqrt{A_0}}{A_0} \quad (1)$$

where $\beta$ is a vessel stiffness index which is a function of modulus of elasticity E, wall thickness $h_0$, and Poisson ratio $\xi$. The term A is representative of cross sectional area of the blood vessel and p is representative of blood pressure value. The term $A_0$ is cross sectional area of the blood vessel at diastole when blood pressure is $p_0$. A is representative of cross sectional area of the blood vessel and p is representative of blood pressure. The vessel-stiffness index is represented by the relation:

$$\beta = \frac{\sqrt{\pi} h_0 E}{1 - \xi^2} \quad (2)$$

Arterial pulse wave velocity c is represented by the relation:

$$c^2 = \frac{A}{\rho} \frac{dp}{dA} \quad (3)$$

where $\rho$ is the density of the blood.

In one embodiment, the optimization technique used by the model generation unit 116, is formulated based on boundary conditions of the blood vessel. A micro circulation resistance of the vessel segment is determined by the relation:

$$R = \frac{Q_{mean}}{p_{mean}} \quad (4)$$

where $Q_{mean}$ is a mean flow rate at an inlet of a blood vessel and $p_{mean}$ is a mean brachial pressure value. The circulation resistance R is also equal to a total resistance of a lumped RCR model represented by $R_1 + R_2$. When there is an impedance matching at the blood vessel-lumped model interface, the resistance $R_1$ is equal to the impedance of the blood vessel represented by the relation:

$$R_1 = \frac{\rho c_0}{A_0} \quad (5)$$

where $c_0$ is the arterial pulse wave velocity at the output of the blood vessel and $A_0$ is the corresponding cross-sectional area. With reference to equations (4), (5), the number of variables in the flow model is reduced to two. The first variable is the vessel compliance value $\beta$ and the second variable is lumped model compliance value C.

In one embodiment, the optimization technique involves using a cost function based on a difference between a plurality of predicted values obtained from the hemodynamic model and a plurality of corresponding measured values obtained from the imaging data set. The cost function is minimized in the optimization to determine unknown variables. In one embodiment, the cost function is based on estimated blood flow rate and the measured blood flow rate values. In an alternate embodiment, the optimization technique involves using a cost function based on the estimated cross sectional area values of the blood vessel and corresponding measured cross sectional area values.

In one embodiment, the mean blood pressure is also obtained during the optimization process without use of a plurality of cuff measurements. In such an embodiment, a plurality of measured cross sectional area values corresponding to a plurality of cardiac phases, is obtained from the imaging data set. A plurality of estimated cross sectional area values corresponding to the plurality of measured cross sectional area values, is obtained from the hemodynamic model. A cost function based on a difference between the measured cross sectional area and the estimated cross sectional area is used in the optimization formulated based on equation (1). The cost function is minimized for a pressure value p in the equation (1) to provide an estimate of the mean blood pressure. The optimization technique involves three variable parameters namely mean blood pressure, blood vessel compliance value, and lumped model compliance value.

The processor module 118 is communicatively coupled to a communication bus and may include at least one of an arithmetic logic unit, a microprocessor, a general purpose controller, and a processor array to perform the desired computations or run the computer programs. In one embodiment, the processor module 118 may be configured to aid the data acquisition unit 110, the image segmentation unit 112, the image processing unit 114, and the model generation unit 116 to perform associated tasks. It may be noted that while the embodiment of FIG. 1 depicts the processor module 118 as a separate unit, in certain embodiments, one or more of the data acquisition unit 110, the image segmentation unit 112, the image processing unit 114, and the model generation unit 116 may include at least one processor module.

In addition, the memory unit 120 is communicatively coupled to the processor module 118 and may be accessed by one or more of the data acquisition unit 110, the image segmentation unit 112, the image processing unit 114, and the model generation unit 116. In an exemplary embodiment, the memory unit 120 may include one or more memory modules. The memory unit 120 may be a non-transitory storage medium. For example, the memory may be a dynamic random access memory (DRAM) device, a static random access memory (SRAM) device, flash memory or other memory devices. In one embodiment, the memory may include a non-volatile memory or similar permanent storage device, media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. In another embodiment, a non-transitory computer readable medium may be encoded with a program having instructions to instruct the processor module 118 to perform functions of the data acquisition unit 110, image segmentation unit 112, the image processing unit 114, the model generation unit 116.

Figure 2A:
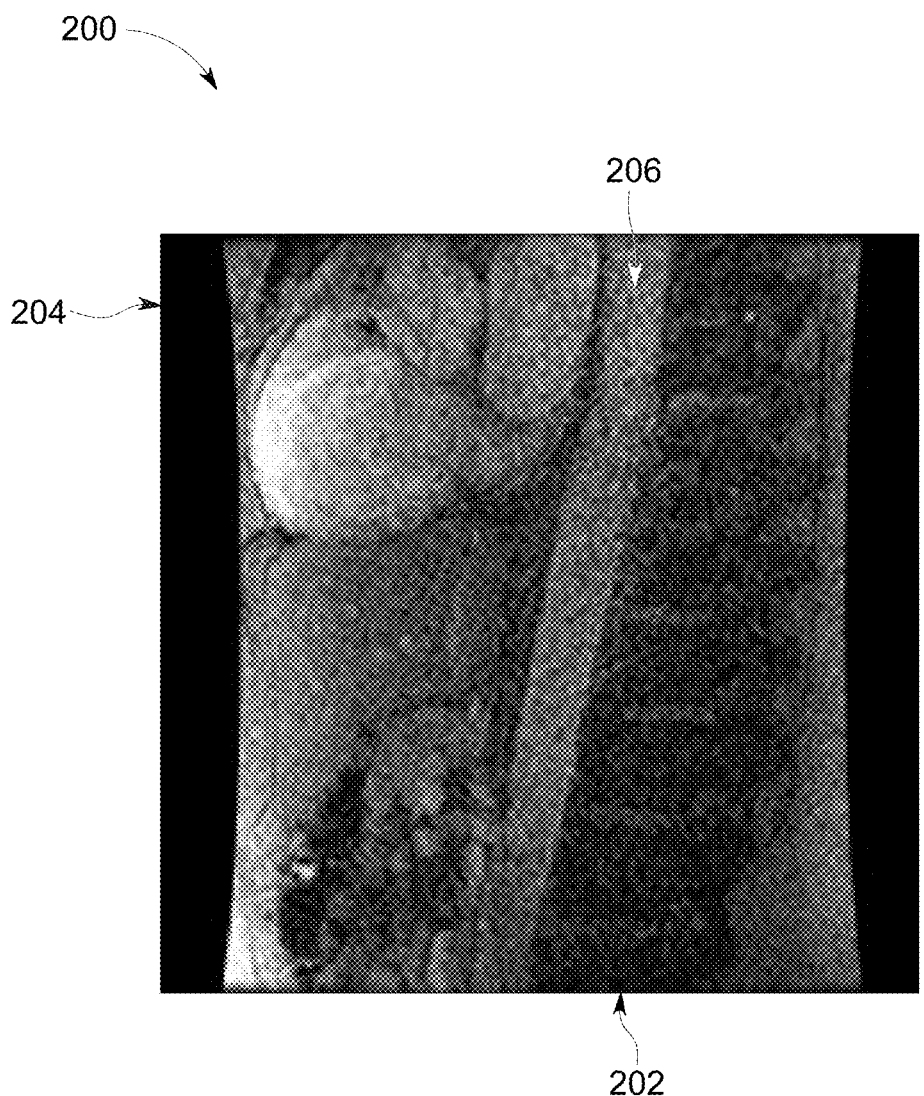
FIG. 2A illustrates magnitude of an image of a blood vessel region, obtained from an imaging modality in accordance with an embodiment of the present invention.

FIG. 2A illustrates an image 200 representative of magnitude of an image from the image data set obtained from an imaging modality in accordance with an embodiment of the present invention. The image 200 includes an X-axis 202 representative of pixel number along the length of the image 200 and a Y-axis 204 representative of pixel number along the width of the image 200. The image 200 is representative of a blood vessel region having a blood vessel 206 for which vessel stiffness parameter is to be determined. The image data set corresponding to the image 200 is obtained from an MRI machine. In alternative embodiments, the image 200 is extracted from image data set obtained from other imaging modalities.

Figure 2B:
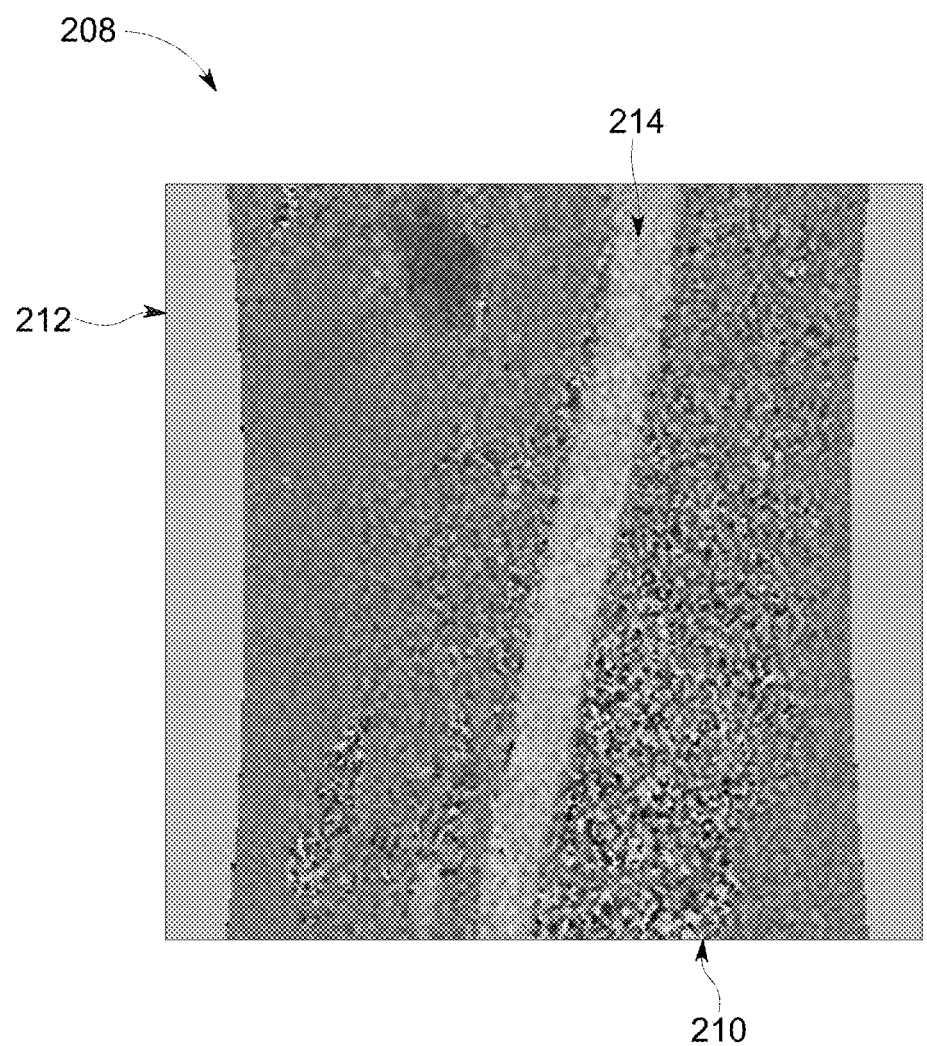
FIG. 2B illustrates phase information of an image of a blood vessel region, obtained from an imaging modality in accordance with an embodiment of the present invention

FIG. 2B illustrates an image 208 representative of phase information of an image 208 from the image data set obtained from an imaging modality in accordance with an embodiment of the present invention. The image 208 includes a X-axis 210 representative of pixel number along the length of the image 208 and a Y-axis 212 representative of pixel number along the width of the image 208. The image 208 is representative of a blood vessel region having a blood vessel 214 for which vessel stiffness parameter is to be determined. The image data set corresponding to the image 208 is obtained from an MRI machine. In alternative embodiments, the image 208 is extracted from an image data set obtained from other imaging modalities.

Figure 3:
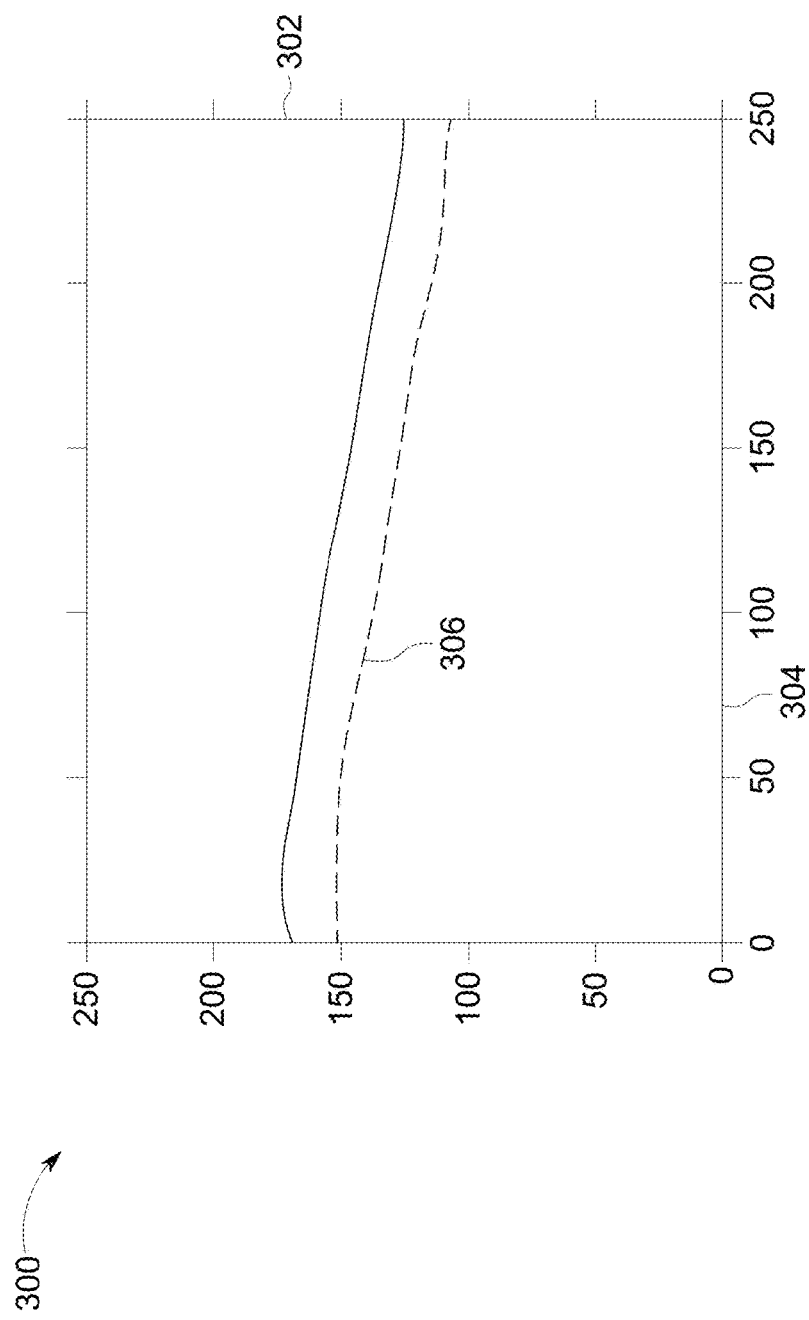
FIG. 3 illustrates a processed image showing an outline of a blood vessel of FIG. 2 in accordance with an embodiment of the present invention.

FIG. 3 illustrates a processed image 300 showing outline of the blood vessel 206 of FIG. 2 in accordance with embodiment of the present invention. X-axis 302 and Y-axis 304 are representative of pixel numbers along the length and the width of the image 300 respectively. The image 300 is obtained by processing the image 200 of FIG. 2 for extracting one or more image parameters required for generating a hemodynamic model. In one embodiment, the processed image 300 is a segmented image having a segmented blood vessel 306. A cross section area of the blood vessel 206 is determined based on the segmented blood vessel 306. In another embodiment, the processed image 300 includes phase information of the cardiac cycle corresponding to the image of FIG. 2 and is used to determine a flow rate of blood flowing within the blood vessel 206.

Figure 4:
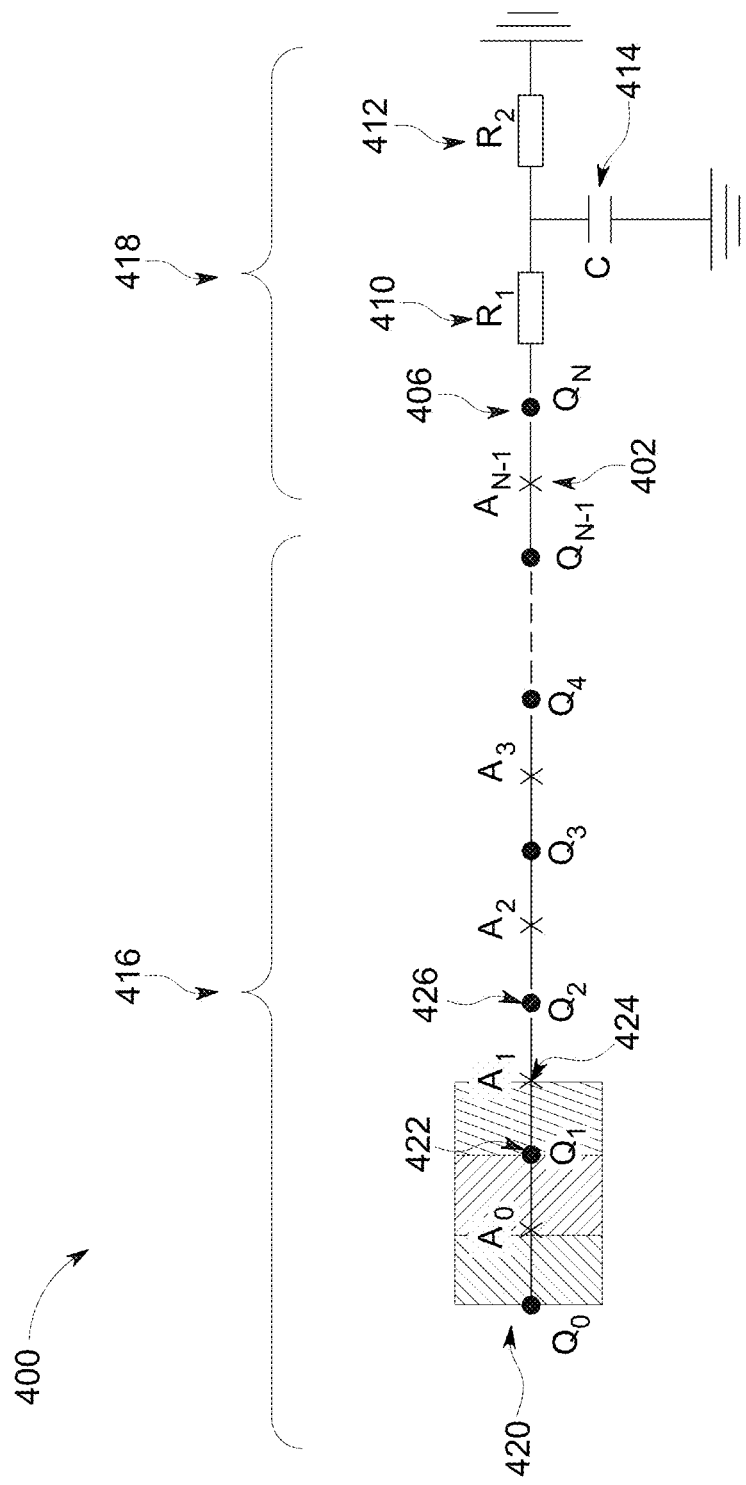
FIG. 4 illustrates a circuit diagram representative of a hemodynamic model in accordance with an embodiment of the present invention.

FIG. 4 illustrates a circuit 400 representative of a hemodynamic model in accordance with an embodiment of the present invention. The hemodynamic model represented by the circuit 400, includes a one dimensional (1D) model 416 coupled to a lumped RCR model 418. The 1D model 416 is representative of propagation of fluid pulse within a blood vessel. The model 416 is based on 1D pulse propagation equations obtained from 3D Navier-Stokes equations. In one embodiment, the 3D Navier-Stokes equations are simplified based on an assumption that fluid pulse wavelength is larger than the diameter of the blood vessel. Equations for conservation of mass and momentum are obtained based on the assumption. A cross-sectional area value of the blood vessel and blood flow rate within the blood vessel are included in the equations for conservation of mass and momentum. A radial velocity profile is used to relate the cross-sectional area and the blood flow rate to a velocity of blood flow along an axis of the blood vessel. In one embodiment, a parabolic velocity profile with parabolic parameters of 0.75 and −4 is used.

A circuit diagram equivalent of lumped RCR model 418 includes input parameter nodes 402, 406 representative of a pressure value and a flow rate respectively of blood entering the blood vessel. A relationship between the input parameter node 402 and the input parameter node 406 is determined by a lumped RCR model 418 having a first resistor 410, a second resistor 412, and a capacitor 414. The capacitor 414 is representative of a vessel compliance value. The parameters of the circuit 400 are obtained by processing of the image FIG. 2 and determining a plurality of parameters corresponding to the blood vessel 206 in.

The momentum and mass conservation equations, the pressure-cross sectional area relationship represented by equation (1) and the equations representing the lumped RCR model 418 constitute a system of non-linear, coupled equations. The pressure-cross sectional area relationship is used to eliminate pressure from the momentum equation. Spatial derivatives are discretized using a second-order accurate central difference scheme. In one embodiment, a staggered approach of discretization is employed. In such an approach, the mass conservation equations are discretized in cells 420, 424. Further, the momentum conservation equations are discretized in cells 422, 426. The cells 420, 424 having interior nodes used for discretization of mass conservation equation is half-cell apart from the cells 424, 426 having interior nodes used for discretization of momentum conservation equation. A time step for discretization is dynamically determined for each time instant. An outlet of the 1D model is a Q node representative of the input parameter node 406. The pressure at 406 is extrapolated from the input parameter node 402. Temporal discretization of the equation representing the lumped RCR model is performed using the low-storage, third-order Runge-Kutta scheme.

Figure 5:
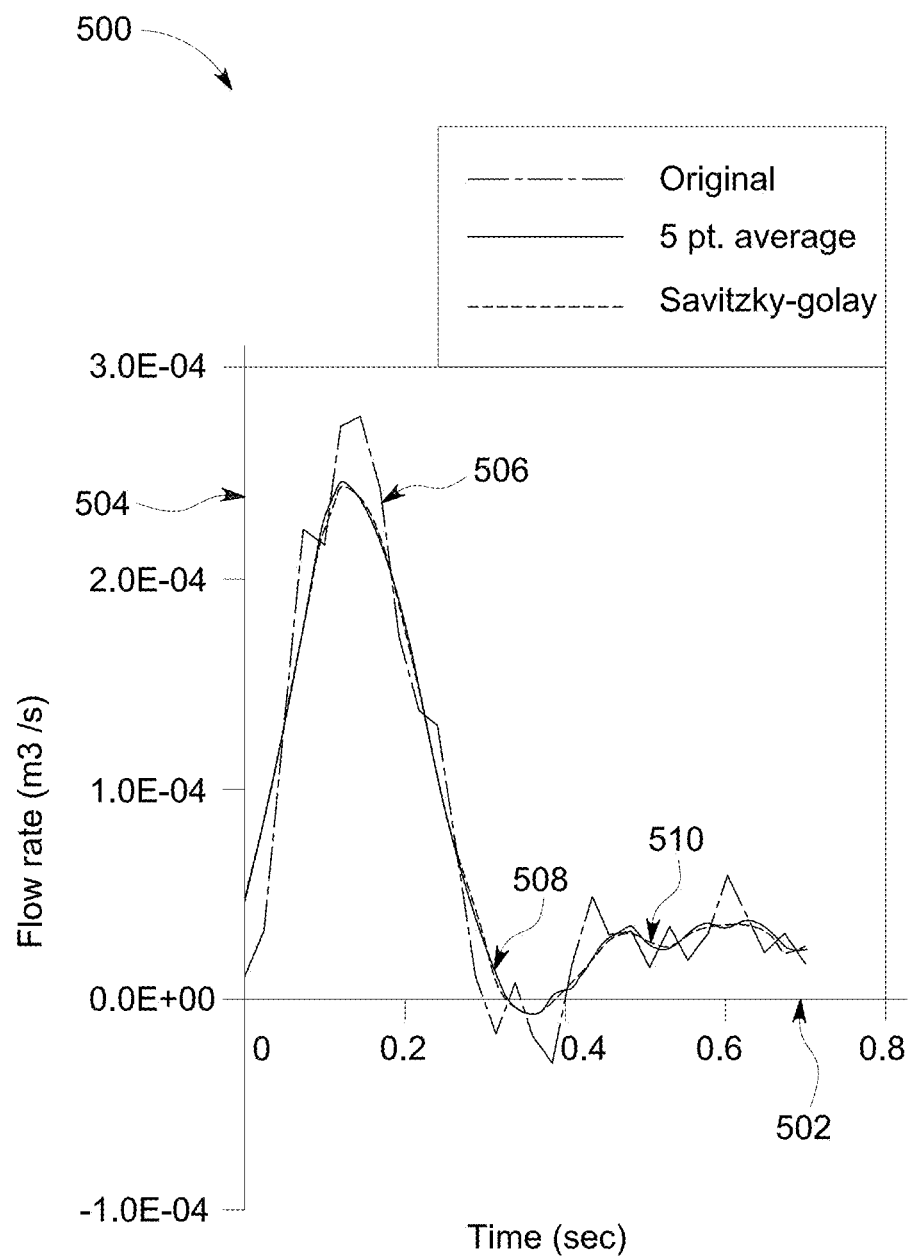
FIG. 5 illustrates a graph representative of blood flow rate obtained from waveform measurements of the image of FIGS. 2A and 2B in accordance with an embodiment of the present invention.

FIG. 5 illustrates a graph 500 representative of a plurality of blood flow rate measurements obtained from the image 200 of FIG. 2 in accordance with an embodiment of the present invention. The graph 500 includes an x-axis 502 representative of time in seconds and a y-axis 504 representative of blood flow rate in cubic meters per second. The graph 500 includes three curves 506, 508, 510 representative of blood flow rates in the blood vessel 206. The curve 506 corresponds to blood flow rate based on velocity data obtained from the image data set in accordance with a first embodiment. The curve 508 corresponds to blood flow rate obtained from smoothed velocity data in accordance with a second embodiment. In such an embodiment, the smoothing process is performed by averaging five data points of the velocity data. The curve 510 corresponds to blood flow rate obtained from smoothed velocity data in accordance with a third embodiment. In such an embodiment, a Savitzy-Golay filter is used to reduce noise in the velocity data. It may be noted that the curve 510 is smooth compared to the curve 506 because the filtering operation reduces the effect of noise in the velocity data.

Figure 6:
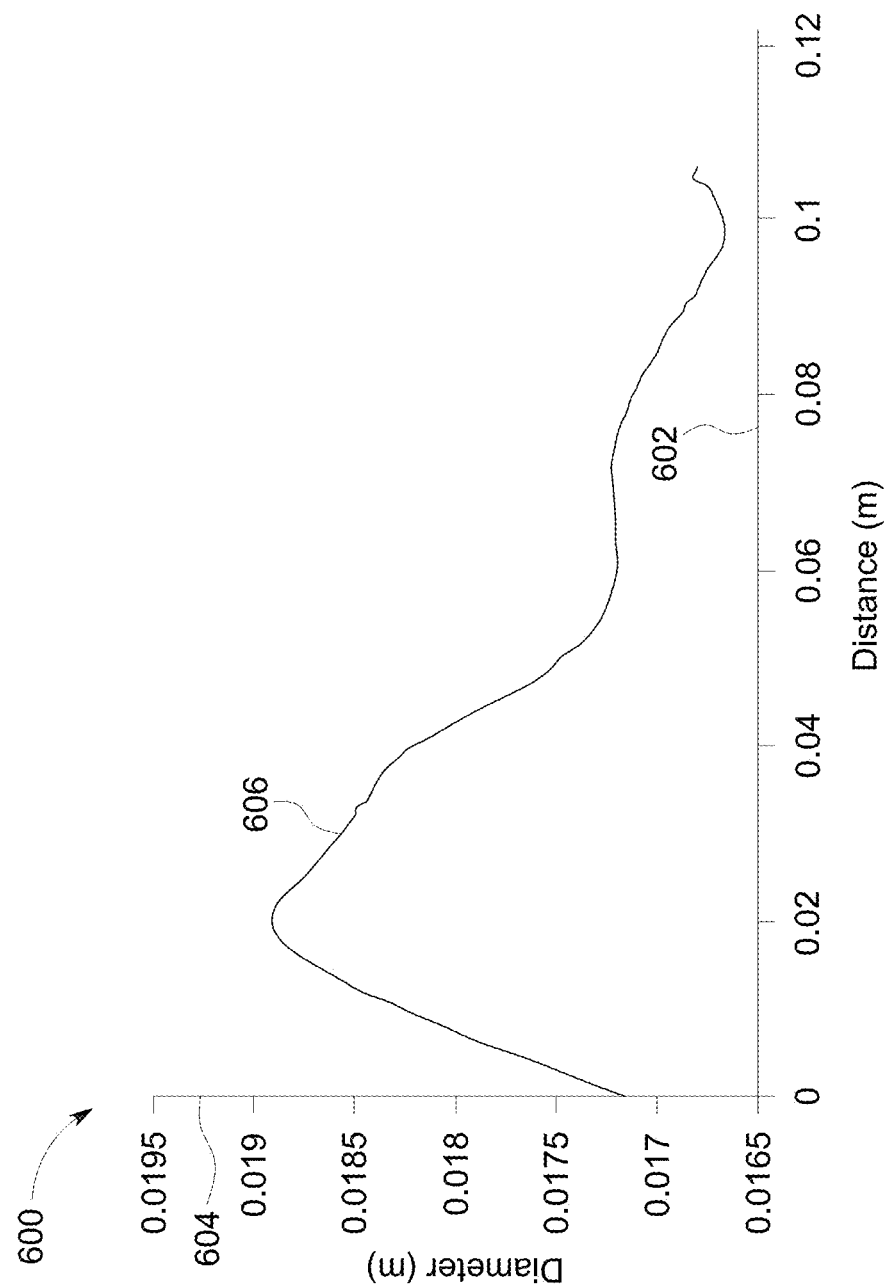
FIG. 6 is a graph illustrating blood-vessel diameter profile along the blood vessel in accordance with an embodiment of the present invention.

FIG. 6 is a graph 600 illustrating diameter profile along a blood vessel in accordance with an embodiment of the present invention. The graph 600 includes an x-axis 602 representative of distance in meters along the blood vessel and a y-axis 604 representative of diameter of the blood vessel in meters for a cardiac cycle. The graph 600 includes a curve 606 representative of cross sectional area of the blood vessel. It may be observed that the diameter of the blood vessel varies along the length of the blood vessel.

Figure 7:
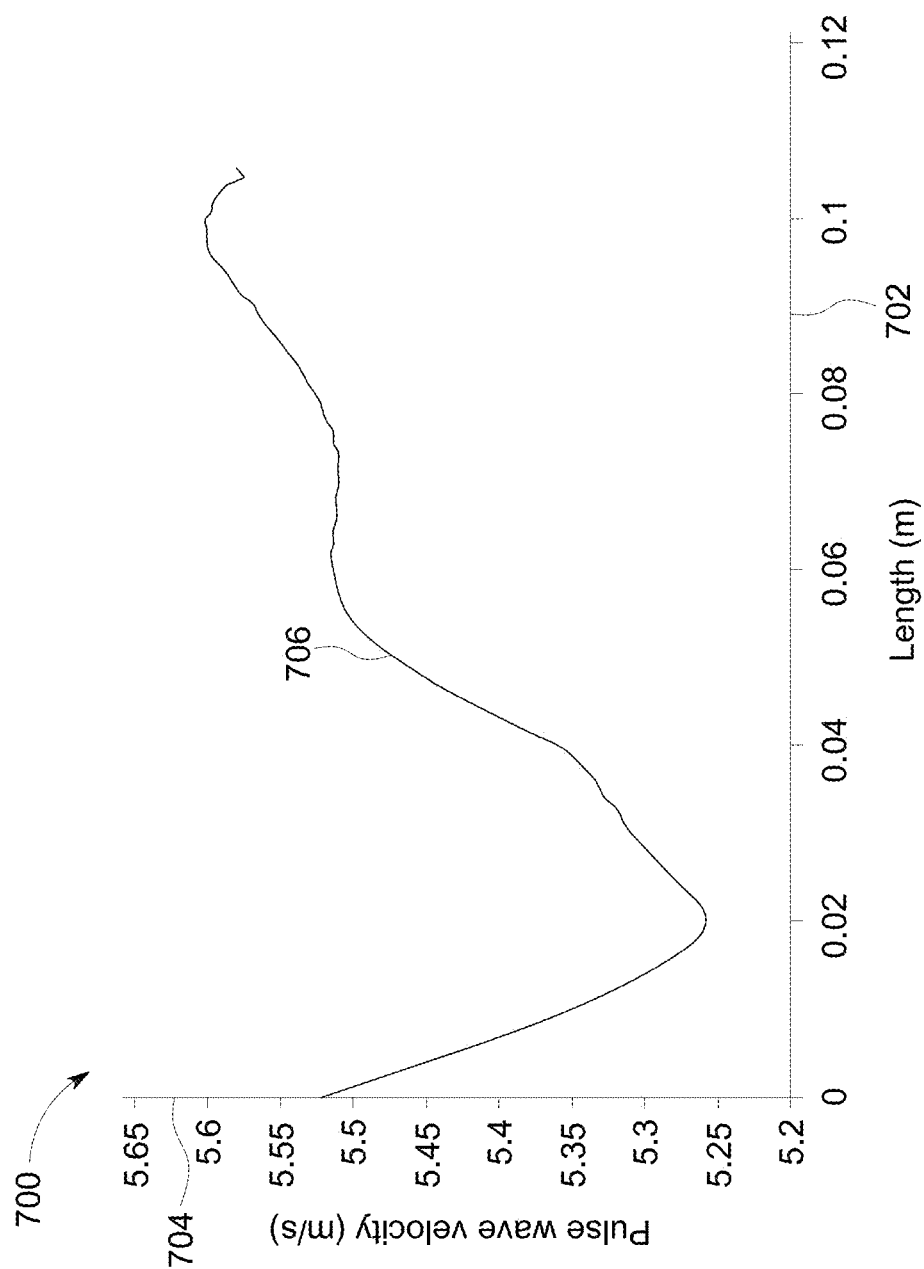
FIG. 7 is a graph 700 illustrating arterial pulse wave velocity profile along the blood vessel in accordance with an embodiment of the present invention.

FIG. 7 is a graph 700 illustrating arterial pulse wave velocity profile along the blood vessel in accordance with an embodiment of the present invention. The graph 700 includes an x-axis 702 representative of distance in meters along the blood vessel and a y-axis 704 representative of arterial pulse wave velocity in the blood vessel in meters per second. The graph 700 includes a curve 706 representative of arterial pulse wave velocity. It may be observed that the arterial pulse wave velocity profile exhibits an inverse relationship compared to the curve 606 representative of cross sectional area profile.

Figure 8:
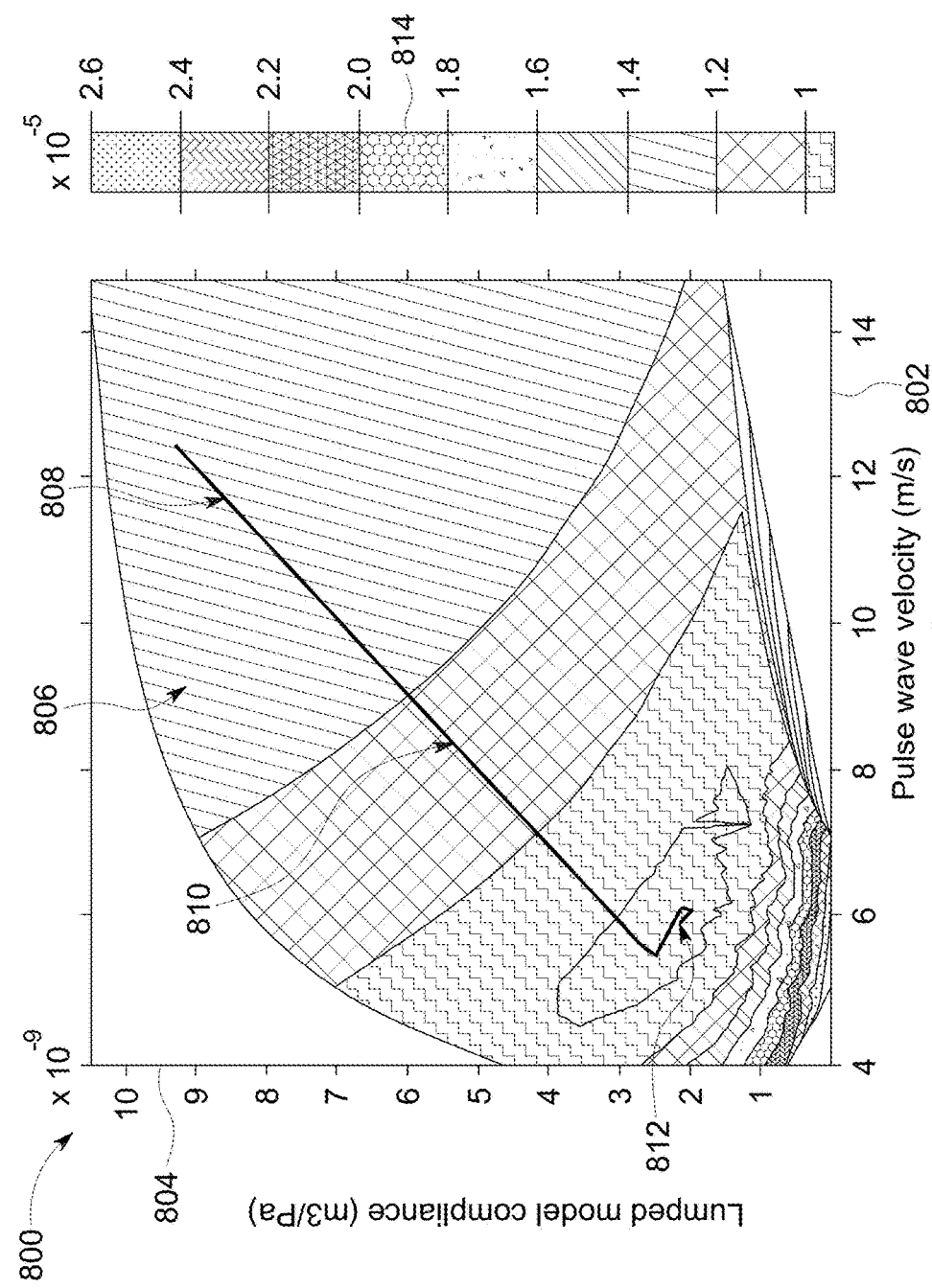
FIG. 8 is a graph illustrating optimization of cost function in accordance with an embodiment of the present invention.

FIG. 8 is a graph 800 illustrating optimization of cost function in accordance with aspects of the present specification. The graph 800 includes an x-axis 802 representative of arterial pulse wave velocity in meters per second and a y-axis 804 representative of blood vessel compliance value in cubic meters per Pascal. An optimization space 806 is representative of a difference between measured flow rates and predicted flow rates at a predefined location. A line 808 is representative of a path of the optimization technique to determine the arterial pulse wave velocity. An optimum point 812 is reached via an intermediate point 810 in the optimization space 806. A shade bar 814 is representative of a plurality of values of the optimization space. It may be observed that with reference to the optimization space 806, a gradient based technique may be used for determining the optimum point 812.

Figure 9:
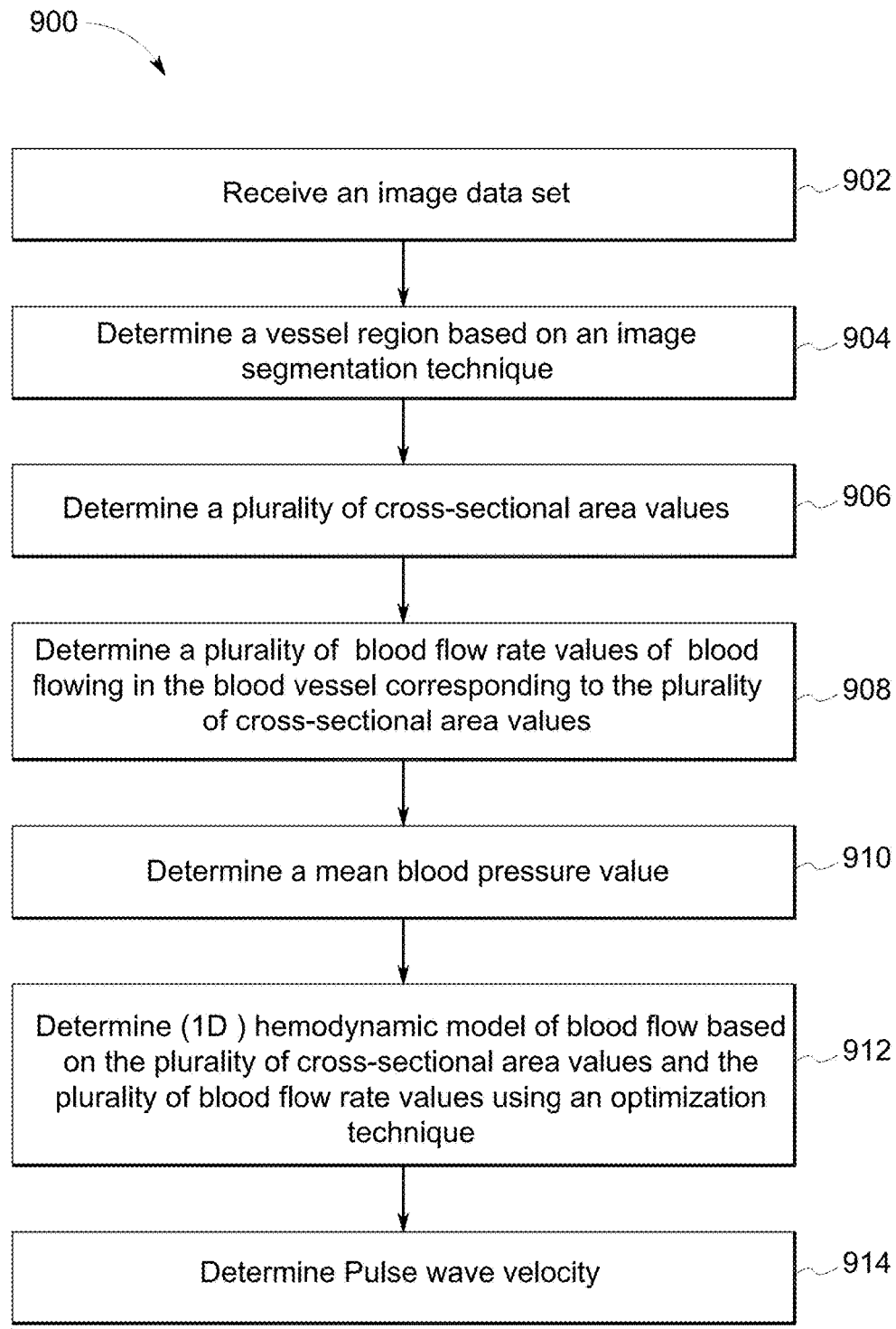
FIG. 9 is a flow chart of a method for estimating arterial pulse wave velocity of blood flow in accordance with an embodiment of the present invention.

FIG. 9 is a flow chart 900 representative of a method for estimating arterial pulse wave velocity of the blood vessel in accordance with an exemplary embodiment. The method includes receiving an image data set of a subject from an imaging modality in step 902. The imaging data set includes a plurality of images. In one embodiment, the image data set is obtained from a magnetic resonance imaging modality. The method further also includes determining a vessel region in an image of the plurality of images based on an image segmentation technique in step 904. In step 906, a vessel centerline is determined. Further, a plurality of cross-sectional area values of a blood vessel in the vessel region is determined, based on the vessel centerline. In one embodiment, the vessel centerline may be obtained from a recursive tracing technique. In another embodiment, an orientation filtering technique may be used to determine the centerline. In one embodiment, the plurality of cross-sectional area values is determined at a plurality of locations along the blood vessel corresponding to a plurality of phases of a cardiac cycle.

The method further includes determining a plurality of blood flow rate values of blood flowing in the blood vessel based on the imaging data set in step 908. In one embodiment, the plurality of flow rate values corresponds to the plurality of cross-sectional area values. In step 910, the method includes determining a mean blood pressure value. In one embodiment, the mean blood pressure value is determined based on a plurality of cuff measurements. In another embodiment, the mean blood pressure value is determined based on an optimization technique without use of the plurality of cuff measurements. In step 912, a hemodynamic model for blood flow is determined based on the plurality of cross-sectional area values and the plurality of flow rate values, using an optimization technique. In one embodiment, determining the hemodynamic model involves determining at least one of a mean blood pressure, a blood vessel compliance value and a lumped model compliance value based on the optimization technique. Finally, at step 914, an arterial pulse wave velocity is determined based on the hemodynamic model is determined. The arterial pulse wave velocity is representative of a health condition of the blood vessel.

Disclosed embodiments enable assessment of arterial vessel stiffness by determining robust estimates of arterial pulse wave velocity. Arterial vessel stiffness increases for various disease states such as atherosclerosis, diabetes and hypertension. In the case of atherosclerosis, the disclosed technique is useful in differentiating local stiffness changes arising from the disease from stiffness changes occurring due to other factors such as aging and thus helping in diagnosis. Further, the disclosed technique helps in detecting the presence of atherosclerotic lesions before they turn symptomatic. Measurement of local stiffness is also useful for selecting atherosclerosis treatment options.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method comprising:
   receiving an image data set comprising a plurality of images of a subject, from an imaging acquisition device;
   determining a blood vessel region in an image from the plurality of images, using an image segmentation technique;
   determining a plurality of cross-sectional area values of a blood vessel at a plurality of locations in the blood vessel region, corresponding to a plurality of phases of a cardiac cycle of the subject;

determining a plurality of flow rate values of blood flowing in the blood vessel corresponding to the plurality of cross-sectional area values, based on the image data set;

determining a hemodynamic model for the blood vessel based on the plurality of cross-sectional area values and the plurality of blood flow rate values; and determining an arterial pulse wave velocity based on the hemodynamic model, wherein the arterial pulse wave velocity is representative of a health condition of the blood vessel.

2. The method of claim 1, wherein receiving an image data set comprises acquiring a magnetic resonance image data set from a magnetic resonance imaging acquisition device, using a velocity-phase encoding gradient field.

3. The method of claim 1, wherein determining a hemodynamic model comprises determining a one dimensional pulse propagation model and a lumped resistance-capacitance-resistance (RCR) model coupled to the one dimensional pulse propagation model.

4. The method of claim 1, wherein the hemodynamic model comprises a three dimensional computation fluid dynamic model and a lumped resistance-capacitance-resistance (RCR) model coupled to the three dimensional computation fluid dynamic model.

5. The method of claim 1, further comprising determining a mean blood pressure based on a plurality of cuff measurements of the subject.

6. The method of claim 1, wherein determining a hemodynamic model comprises determining at least one of a mean blood pressure, a blood vessel compliance value, and a lumped model compliance value based on a gradient descent technique.

7. The method of claim 6, wherein the gradient descent technique comprises using a cost function based on a difference between a plurality of predicted values obtained from the hemodynamic model and a plurality of corresponding measured values obtained from the imaging data set.

8. The method of claim 7, wherein the corresponding measured values are the cross-sectional area values of the blood vessel.

9. The method of claim 7, wherein the corresponding measured values are the blood flow rate values of the blood vessel.

10. A system comprising:
an imaging acquisition device;
a processor coupled to the imaging acquisition device and configured to:
  receive an image data set comprising a plurality of images of a subject, from the imaging acquisition device;
  determine a blood vessel region in an image from the plurality of images, using an image segmentation technique;
  determine a plurality of cross-sectional area values of a blood vessel, at a plurality of locations in the blood vessel region corresponding to a plurality of phases of a cardiac cycle of the subject;
  determine a plurality of flow rate values of blood flowing in the blood vessel corresponding to the plurality of cross-sectional area values, based on the image data set;
  determine a hemodynamic model for the blood vessel based on the plurality of cross-sectional area values and the plurality of blood flow rate values; and
  determine an arterial pulse wave velocity based on the hemodynamic model, wherein the arterial pulse wave velocity is representative of a health condition of the blood vessel.

11. The system of claim 10, wherein the imaging acquisition device is a magnetic resonance imaging acquisition device.

12. The system of claim 10, wherein the processor is configured to determine the hemodynamic model comprising a one dimensional pulse propagation model and a lumped resistance-capacitance-resistance (RCR) model coupled to the one dimensional pulse propagation model.

13. The system of claim 10, wherein processor is configured to determine the hemodynamic model comprising a three dimensional computation fluid dynamic model and a lumped resistance-capacitance-resistance (RCR) model coupled to the three dimensional computation fluid dynamic model.

14. The system of claim 10, wherein processor is configured to determine a mean blood pressure value based on a plurality of cuff measurements.

15. The system of claim 10, wherein processor is configured to determine the hemodynamic model by determining at least one of a mean blood pressure value, a blood vessel compliance value, and a lumped model compliance value based on a gradient descent technique.

16. The system of claim 15, wherein the processor is configured to perform the gradient descent technique using a cost function based on a difference between a plurality of predicted values obtained from the hemodynamic model and a plurality of corresponding measured values obtained from the imaging data set.

17. The system of claim 16, wherein the corresponding measured values are the cross-sectional area values of the blood vessel.

18. The system of claim 16, wherein the corresponding measure values are the blood flow rate values of the blood vessel.

19. A non-transitory computer readable medium having instructions to enable at least one processor to:
receive an image data set comprising a plurality of images of a subject, from an imaging acquisition device;
determine a blood vessel region in an image from the plurality of images, using an image segmentation technique;
determine a plurality of cross-sectional area values of a blood vessel at a plurality of locations in the blood vessel region corresponding to a plurality phases of a cardiac cycle of the subject;
determine a plurality of flow rate values of blood flowing in the blood vessel corresponding to the plurality of cross-sectional area values, based on the image data set;
determine a hemodynamic model for the blood vessel based on the plurality of cross-sectional area values and the plurality of blood flow rate values; and
determine an arterial pulse wave velocity based on the hemodynamic model, wherein the arterial pulse wave velocity is representative of a health condition of the blood vessel.

* * * * *